United States Patent
Mansfield et al.

(10) Patent No.: US 8,148,538 B2
(45) Date of Patent: Apr. 3, 2012

(54) N-ALKYL-HETEROCYCLYL CARBOXAMIDE DERIVATIVES

(75) Inventors: Darren Mansfield, Bergisch Gladbach (DE); Pierre-Yves Coqueron, Lyons (FR); Heiko Rieck, Burscheid (DE); Philippe Desbordes, Lyons (FR); Alain Villier, Collonges au Mont d'Or (FR); Marie-Claire Grosjean-Cournoyer, Curis au Mont d'Or (FR); Pierre Genix, Lyons (FR)

(73) Assignee: Bayer Cropscience AG (DE)

( * ) Notice: Subject to any disclaimer, the term of this patent is extended or adjusted under 35 U.S.C. 154(b) by 473 days.

(21) Appl. No.: 12/083,123

(22) PCT Filed: Oct. 4, 2006

(86) PCT No.: PCT/EP2006/067013
§ 371 (c)(1),
(2), (4) Date: Apr. 4, 2008

(87) PCT Pub. No.: WO2007/039615
PCT Pub. Date: Apr. 12, 2007

(65) Prior Publication Data
US 2010/0197633 A1    Aug. 5, 2010

(30) Foreign Application Priority Data
Oct. 5, 2005 (EP) .................... 05356179

(51) Int. Cl.
| A01N 55/10 | (2006.01) |
| A01N 43/56 | (2006.01) |
| C07F 5/02 | (2006.01) |
| C07D 231/10 | (2006.01) |
| A01P 3/00 | (2006.01) |

(52) U.S. Cl. ........ 548/110; 548/374.1; 514/63; 514/406
(58) Field of Classification Search .................. None
See application file for complete search history.

(56) References Cited

U.S. PATENT DOCUMENTS

| 5,021,081 | A | * | 6/1991 | Findeisen et al. ............. 504/273 |
| 5,240,951 | A | | 8/1993 | Shimotori et al. |
| 5,451,702 | A | | 9/1995 | Stern et al. |
| 2003/0199536 | A1 | * | 10/2003 | Thomas et al. ............... 514/285 |
| 2005/0049237 | A1 | * | 3/2005 | Atkinson et al. ............. 514/210.2 |
| 2005/0059657 | A1 | * | 3/2005 | Cavicchioli et al. ........ 514/227.8 |

FOREIGN PATENT DOCUMENTS

| GB | 1387652 | 3/1975 |
| JP | 09 176124 | 7/1997 |
| JP | 09 188662 A | 7/1997 |
| WO | WO 96/29871 | 10/1996 |
| WO | WO 96/38419 | 12/1996 |
| WO | WO 03/013517 | 2/2003 |

OTHER PUBLICATIONS

Martell et al. in Coordination Chemistry Reviews, vol. 133, Jul. 1994, pp. 39-65.*
Patani et al. in Chemical Reviews 1996, 3147-3176.*
Cantrill, A.A., et al.: "Preparation and Ring-Opening Reactions of N-Diphenylphosphinyl Aziridines", Tetrahedron, Elsevier Science Publishers, Amsterdam, NL, vol. 54, No. 10, Mar. 5, 1998, pp. 2181-2208, XP004109555, ISSN: 0040-4020.
Patent Abstracts of Japan, vol. 1997, No. 11, Nov. 28, 1997 & JP 09 176124 A (Nissan Chem, Ind. Ltd.), Jul. 8, 1997.
Thomas et al.: "Synthesis of long-chain amide analogs of the cannabinoid CB1 receptor antagonist N-(piperidinyl)-5-(4-chlorophenyl)-1-(2,4-dichlorophenyl)-4-methyl-1H-pyrazole-3-calboxamide (SR141716) with unique binding selectivities and pharmacological activities", Bioorganic & Medicinal Chemistry, Elsevier Science Ltd., GB, vol. 13, No. 18, Sep. 18, 2005, pp. 5463-5474, XP005021048.
Database CAPLUS [Online], Chemical Abstracts Service, 1997, XP002375266, Database Accession No. 1363, abstract & JP 09 188662 A (Sumitomo Chem. Co., Ltd.), Jul. 22, 1997.

* cited by examiner

*Primary Examiner* — Timothy Thomas
*Assistant Examiner* — Dennis Heyer
(74) *Attorney, Agent, or Firm* — Ostrolenk Faber LLP

(57) ABSTRACT

A compound of general formula (I):

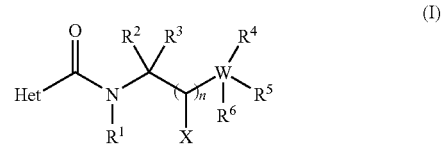

A process for preparing this compound.
A compound of general formula (II)

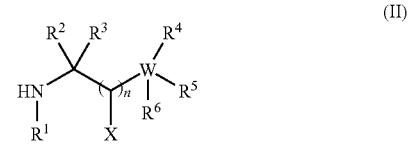

A fungicide composition comprising a compound of general formula (I).
A method for treating plants by applying a compound of general formula (I) or a composition comprising it.

12 Claims, No Drawings

N-ALKYL-HETEROCYCLYL CARBOXAMIDE DERIVATIVES

CROSS REFERENCE TO RELATED APPLICATION(S)

The present application is a 35 U.S.C. §371 national phase conversion of PCT/EP2006/067013 filed 4 Oct. 2006, which claims priority of European Application No. 05356179.1 filed 5 Oct. 2005.

The present invention relates to novel N-alkyl-heterocyclyl carboxamide derivatives, their process of preparation, their use as fungicides, particularly in the form of fungicidal compositions, and methods for the control of phytopathogenic fungi of plants using these compounds or their compositions.

International patent application WO 96/38419 discloses pyrazole carboxamide derivatives of general formula encompassing the compounds according to the present invention, and their use as fungicide. However, compounds according to the present invention are not disclosed in that patent application.

International patent application WO 96/29871 discloses thiadiazole carboxamide derivatives of general formula encompassing the compounds according to the present invention, and their use as fungicide. However, compounds according to the present invention are not disclosed in that patent application.

Great Britain patent application GB 1387652 discloses furan carboxamide derivatives of general formula encompassing the compounds according to the present invention, and their use as fungicide. However, compounds according to the present invention are not disclosed in that patent application.

Japanese patent application JP 9176124 discloses pyrazolin carboxamide derivatives of general formula encompassing the compounds according to the present invention, and their use as fungicide. However, compounds according to the present invention are not disclosed in that patent application.

U.S. Pat. No. 5,240,951 discloses isothiazole carboxamide derivatives of general formula encompassing the compounds according to the present invention, and their use as fungicide. However, compounds according to the present invention are not disclosed in that patent application.

It is always of high-interest in the field of agrochemicals to use pesticidal compounds more active than the compounds already known by the man ordinary skilled in the art whereby less compound can be used whilst retaining equivalent efficacy.

Furthermore, the provision of new pesticidal compounds with a higher efficacy strongly reduces the risk of appearance of resistant strains in the fungi to be treated.

We have now found a new family of compounds which show enhanced fungicidal activity over the general known family of such compounds.

Accordingly, the present invention relates to a N-alkyl-heterocyclyl carboxamide derivative of general formula (I)

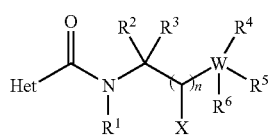

(I)

in which:
Het represents 5-membered non-fused heterocycle with one, two or three heteroatoms which may be the same or different, Het being linked by a carbon atom and being at least substituted in ortho position;
n is 2, 3 or 4;
$R^1$ is chosen as being a hydrogen atom, a $C_1$-$C_6$-alkyl group or a $C_3$-$C_7$-cycloalkyl;
$R^2$ is chosen as being a $C_1$-$C_6$-alkyl group;
$R^3$ is chosen as being a hydrogen atom or a $C_1$-$C_6$-alkyl group;
each X is chosen, independently of the others, as being a hydrogen atom or a $C_1$-$C_6$-alkyl group;
W represents a carbon atom or a silicon atom;
$R^4$, $R^5$ and $R^6$ are chosen, independently of each other, as being a hydrogen atom, a halogen atom, or a $C_1$-$C_6$-alkyl group, at least two of the substituents $R^4$, $R^5$ and $R^6$ being different from a hydrogen atom;
or two of the substituents $R^4$, $R^5$ and $R^6$ may together form a 3-, 4-, 5- or 6-membered non aromatic cycle optionally substituted with a $C_1$-$C_6$-alkyl group;
as well as its salts, N-oxydes, metallic complexes, metalloidic complexes and optically active isomers
with the exception of:
5-(dimethylamino)-N-(1,5-dimethylhexyl)-4-methyl-4H-1,2,4-triazole-3-carboxamide;
N-(1,5-dimethylhexyl)-1-[4-[[(1,5-dimethylhexyl)amino] sulfonyl]phenyl]-4-[[4-[[(1,5-dimethylhexyl)amino]sulfonyl]phenyl]azo]-5-hydroxy-1H-pyrazole-3-carboxamide;
5-amino-N-(1,5-dimethylhexyl)-3-{5-[3-(trifluoromethyl) phenyl]-2-furyl}isoxazole-4-carboxamide;
5-amino-3-bromothien-2-yl)-N-(1,5-dimethylhexyl)isoxazole-4-carboxamide;
5-amino-N-(1,5-dimethylhexyl)-3-(5-methylthien-2-yl) isoxazole-4-carboxamide;
5-amino-N-(1,5-dimethylhexyl)-3-(3-methylthien-2-yl) isoxazole-4-carboxamide;
5-amino-3-[5-(3-chlorophenyl)-2-furyl]-N-(1,5-dimethylhexyl)isoxazole-4-carboxamide;
5-amino-N-(1,5-dimethyl hexyl)-3-(5-methyl-2-furyl)isoxazole-4-carboxamide;
5-amino-N-(1,5-dimethyl hexyl)-3-(2-furyl)isoxazole-4-carboxamide;
5-amino-3-(1-benzofuran-3-yl)-N-(1,5-dimethylhexyl)isoxazole-4-carboxamide;
5-amino-N-(1,5-dimethylhexyl)-3-(5-ethylthien-2-yl)isoxazole-4-carboxamide;
5-amino-3-(5-chloro-2-furyl)-N-(1,5-dimethylhexyl)isoxazole-4-carboxamide;
5-amino-N-(1,5-dimethylhexyl)-3-(6-methoxypyridin-3-yl) isoxazole-4-carboxamide;
5-amino-N-(1,5-dimethylhexyl)-3-pyridin-3-yl)isoxazole-4-carboxamide;
5-(4-chlorophenyl)-1-(2,4-dichlorophenyl)-N-(1,4-dimethylpentyl)-4-methyl-1H-pyrazole-3-carboxamide; and
5-(4-chlorophenyl)-1-(2,4-dichlorophenyl)-N-(1,5-dimethylhexyl)-4-methyl-1H-pyrazole-3-carboxamide.

In the context of the present invention:
halogen means fluorine, bromine, chlorine or iodine.
carboxy means —C(=O)OH; carbonyl means —C(=O)—; carbamoyl means —C(=O)NH$_2$; N-hydroxycarbamoyl means —C(=O)NHOH;
an alkyl group, an alkenyl group, and an alkynyl group as well as moieties containing these terms, can be linear or branched.

In the context of the present invention, it has also to be understood that in the case of di-substituted amino and of di-substituted carbamoyl radicals, the two substituents may form together with the nitrogen atom bearing them a saturated heterocyclic ring containing 3 to 7 atoms.

Any of the compound of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compound of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

According to the present invention, "Het" of the compound of general formula (I) is a 5-membered non-fused heterocycle with one, two or three heteroatoms which may be the same or different, Het being linked by a carbon atom and being at least substituted in ortho position. Preferably, the present invention relates to N-alkyl-heterocyclyl carboxamide derivative of general formula (I) in which the different characteristics may be chosen alone or in combination as being:

as regards Het moiety, Het is chosen as being 2-furan, 3-furan, 4,5-dihydro-3-furan, 2-thiophene, 3-thiophene, 2-pyrrole, 3-pyrrole, 5-oxazole, 4-oxazole, 5-thiazole, 4-thiazole, 5-pyrazole, 4-pyrazole, 3-pyrazole, 3-isoxazole, 4-isoxazole, 5-isoxazole, 3-isothiazole, 4-1,2,3-triazole, 4-thiadiazole or 5-thiadiazole;

as regards the substituents of the "Het" moiety, each substituent is chosen, independently of the others, as being a hydrogen atom, a halogen atom, an amino group, a cyano group, a $C_1$-$C_4$-alkylamino, a di-($C_1$-$C_4$-alkyl)amino, a $C_1$-$C_4$-alkyl, a $C_1$-$C_4$-halogenalkyl having 1 to 5 halogen atoms, a $C_1$-$C_4$-halogenoalkoxy having 1 to 5 halogen atoms, a nitro group, a $C_1$-$C_4$-alkyloxy, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl, a carbamoyl group or an a $C_1$-$C_8$-alkylcarbonylamino, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl or a $C_1$-$C_4$-halogenoalkoxy-$C_1$-$C_4$-alkyl having 1 to 5 halogen atoms;

as regards the substituent in 2-position of the "Het" moiety, the substituent in ortho position of the "Het" moiety is chosen as being a halogen atom, a $C_1$-$C_4$-alkyl, a $C_1$-$C_4$-halogenoalkyl having 1 to 5 halogen atoms, a $C_1$-$C_4$-halogenoalkoxy having 1 to 5 halogen atoms or a $C_1$-$C_4$-alkyloxy;

Specific examples of Het moiety include:

Het represents a heterocycle of the general formula (Het-1)

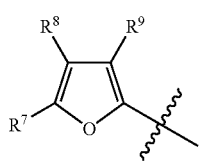

(Het-1)

in which:

$R^7$ and $R^8$ may be the same or different and may be a hydrogen atom, a halogen atom, an amino group, a nitro group, a $C_1$-$C_4$-alkyl or a $C_1$-$C_4$-halogenoalkyl having 1 to 5 halogen atoms; and $R^9$ may be a halogen atom, a nitro group, a $C_1$-$C_4$-alkyl or a $C_1$-$C_4$-halogenoalkyl having 1 to 5 halogen atoms.

Het represents a heterocycle of the general formula (Het-2)

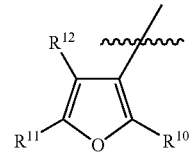

(Het-2)

in which:

$R^{10}$ may be a hydrogen atom, a halogen atom, a $C_1$-$C_4$-alkyl or a $C_1$-$C_4$-halogenoalkyl having 1 to 5 halogen atoms; and $R^{11}$ and $R^{12}$ may be the same or different and may be a hydrogen atom, a halogen atom, an amino group, a $C_1$-$C_4$-alkyl or a $C_1$-$C_4$-halogenoalkyl having 1 to 5 halogen atoms;

provided that the $R^{10}$ and $R^{12}$ are not both a hydrogen atom.

Het represents a heterocycle of the general formula (Het-3)

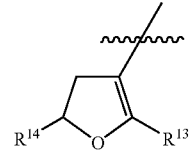

(Het-3)

in which:

$R^{13}$ may be a halogen atom, a $C_1$-$C_4$-alkyl or a $C_1$-$C_4$-halogenoalkyl having 1 to 5 halogen atoms; and $R^{14}$ may be a hydrogen atom, a $C_1$-$C_4$-alkyl or a $C_1$-$C_4$-halogenoalkyl having 1 to 5 halogen atoms.

Het represents a heterocycle of the general formula (Het-4)

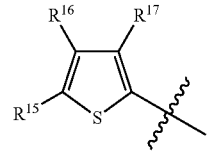

(Het-4)

in which:

$R^{15}$ and $R^{16}$ may be the same or different and may be a hydrogen atom, a halogen atom, a $C_1$-$C_4$-alkyl, a $C_1$-$C_4$-halogenoalkyl having 1 to 5 halogen atoms, a $C_1$-$C_4$-alkylthio, a $C_1$-$C_4$-alkylsulphonyl, a phenyl optionally substituted by a halogen atom or a $C_1$-$C_4$-alkyl or a pyridyl optionally substituted by a halogen atom or a $C_1$-$C_4$-alkyl; and $R^{17}$ may be a halogen atom, a cyano group, a $C_1$-$C_4$-alkyl, a $C_1$-$C_4$-halogenoalkyl having 1 to 5 halogen atoms or a $C_1$-$C_4$-halogenoalkoxy having 1 to 5 halogen atoms.

Het represents a heterocycle of the general formula (Het-5)

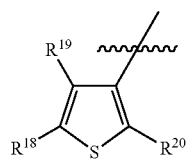

(Het-5)

in which:
$R^{18}$ and $R^{19}$ may be the same or different and may be a hydrogen atom, a halogen atom, a $C_1$-$C_4$-alkyl, a $C_1$-$C_4$-alkyloxy or a $C_1$-$C_4$-halogenoalkyl having 1 to 5 halogen atoms; and $R^{20}$ may be a hydrogen atom, a halogen atom, a $C_1$-$C_4$-alkyl or a $C_1$-$C_4$-halogenoalkyl having 1 to 5 halogen atoms;

provided that the $R^{19}$ and $R^{20}$ are not both a hydrogen atom.

Het represents a heterocycle of the general formula (Het-6)

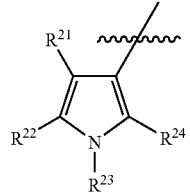

(Het-6)

in which:
$R^{21}$ may be a hydrogen atom, a halogen atom, a cyano group, a $C_1$-$C_4$-alkyl or a $C_1$-$C_4$-halogenoalkyl having 1 to 5 halogen atoms;

$R^{22}$ and $R^{24}$ may be the same or different and may be a hydrogen atom, a halogen atom, a $C_1$-$C_4$-alkyl or a $C_1$-$C_4$-halogenoalkyl having 1 to 5 halogen atoms; and $R^{23}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl;

provided that the $R^{21}$ and $R^{24}$ are not both a hydrogen atom.

Het represents a heterocycle of the general formula (Het-7)

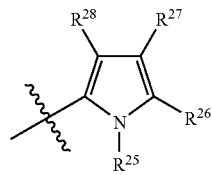

(Het-7)

in which:
$R^{25}$ may be a hydrogen atom, a cyano group, a $C_1$-$C_4$-alkyl, a $C_1$-$C_4$-halogenoalkyl having 1 to 5 halogen atoms, a $C_1$-$C_4$-alkoxy-$C_1$-$C_4$-alkyl, a hydroxy-$C_1$-$C_4$-alkyl, a $C_1$-$C_4$-alkylsulphonyl, a di($C_1$-$C_4$-alkyl)aminosulphonyl, a $C_1$-$C_6$-alkylcarbonyl, a phenylsulphonyl optionally substituted by a halogen atom or a $C_1$-$C_4$-alkyl, or a benzoyl optionally substituted by a halogen atom or a $C_1$-$C_4$-alkyl; and $R^{26}$, $R^{27}$ and $R^{28}$ may be the same or different and may be a hydrogen atom, a halogen atom, a cyano group, a $C_1$-$C_4$-alkyl, a $C_1$-$C_4$-halogenoalkyl having 1 to 5 halogen atoms or a $C_1$-$C_4$-alkylcarbonyl;

provided that $R^{25}$ and $R^{28}$ are not both a hydrogen atom.

Het represents a heterocycle of the general formula (Het-8)

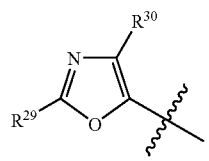

(Het-8)

in which:
$R^{29}$ may be a hydrogen atom or a $C_1$-$C_4$-alkyl; and $R^{30}$ may be a halogen atom, a $C_1$-$C_4$-alkyl or a $C_1$-$C_4$-halogenoalkyl having 1 to 5 halogen atoms.

Het represents a heterocycle of the general formula (Het-9)

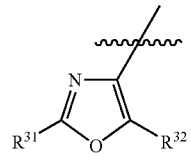

(Het-9)

in which:
$R^{31}$ may be a hydrogen atom or a $C_1$-$C_4$-alkyl; and $R^{32}$ may be a halogen atom, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl.

Het represents a heterocycle of the general formula (Het-10)

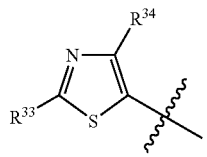

(Het-10)

in which:
$R^{33}$ may be a hydrogen atom, a halogen atom, an amino group, a cyano group, a $C_1$-$C_4$-alkylamino, a di-($C_1$-$C_4$-alkyl)amino, a $C_1$-$C_4$-alkyl, a $C_1$-$C_4$-halogenoalkyl having 1 to 5 halogen atoms or a phenyl optionally substituted by a halogen atom or a $C_1$-$C_4$-alkyl; and $R^{34}$ may be a halogen atom, a $C_1$-$C_4$-alkyl or a $C_1$-$C_4$-halogenoalkyl having 1 to 5 halogen atoms.

Het represents a heterocycle of the general formula (Het-11)

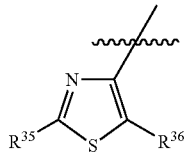

(Het-11)

in which:
R$^{35}$ may be a hydrogen atom, a halogen atom, an amino group, a cyano group, a C$_1$-C$_4$-alkylamino, a di-(C$_1$-C$_4$-alkyl)amino, a C$_1$-C$_4$-alkyl or a C$_1$-C$_4$-halogenoalkyl having 1 to 5 halogen atoms; and
R$^{36}$ may be a halogen atom, a C$_1$-C$_4$-alkyl or a C$_1$-C$_4$-halogenoalkyl having 1 to 5 halogen atoms.

Het represents a heterocycle of the general formula (Het-12)

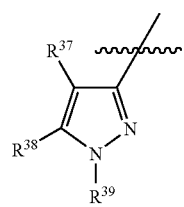

(Het-12)

in which:
R$^{37}$ may be a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl group or an aminocarbonyl-C$_1$-C$_4$-alkyl;
R$^{38}$ may be a hydrogen atom, a halogen atom, a cyano group, a nitro group, a C$_1$-C$_4$-alkyl, a C$_1$-C$_4$-alkoxy or a C$_1$-C$_4$-alkylthio; and
R$^{39}$ may be a hydrogen atom, a phenyl, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl or a C$_1$-C$_4$-halogenoalkoxy-C$_1$-C$_4$-alkyl having 1 to 5 halogen atoms.

Het represents a heterocycle of the general formula (Het-13)

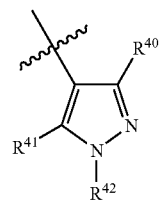

(Het-13)

in which:
R$^{40}$ may be a hydrogen atom, a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl or an aminocarbonyl-C$_1$-C$_4$-alkyl;
R$^{41}$ may be a hydrogen atom, a halogen atom, a cyano group, a C$_1$-C$_4$-alkyl, a C$_1$-C$_4$-alkoxy, a C$_1$-C$_4$-halogenoalkoxy having 1 to 5 halogen atoms or a C$_1$-C$_4$-alkylthio; and
R$^{42}$ may be a hydrogen atom, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl, a C$_1$-C$_4$-halogenoalkoxy-C$_1$-C$_4$-alkyl having 1 to 5 halogen atoms or a phenyl optionally substituted by a halogen atom, a C$_1$-C$_4$-alkyl, a C$_1$-C$_4$-alkoxyalkyl or a nitro group;
provided that the R$^{40}$ and R$^{41}$ are not both a hydrogen atom.

Het represents a heterocycle of the general formula (Het-14)

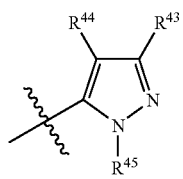

(Het-14)

in which:
R$^{43}$ may be a hydrogen atom, a halogen atom, a cyano group, a nitro group, a C$_1$-C$_4$-alkyl, a C$_1$-C$_4$-halogenoalkyl having 1 to 5 halogen atoms, a C$_3$-C$_6$-cycloalkyl, a C$_1$-C$_4$-alkoxy, a C$_1$-C$_4$-halogenoalkoxy having 1 to 5 halogen atoms, a C$_1$-C$_4$-alkylthio, a C$_1$-C$_4$-halogenoalkylthio having 1 to 5 halogen atoms, an aminocarbonyl, or an aminocarbonyl-C$_1$-C$_4$-alkyl;
R$^{44}$ may be a hydrogen atom, a halogen atom, a cyano group, a C$_1$-C$_4$-alkyl, a C$_1$-C$_4$-alkoxy, a C$_1$-C$_4$-alkylthio or a C$_1$-C$_4$-halogenoalkyl having 1 to 5 halogen atoms;
R$^{45}$ may be a hydrogen atom, a phenyl, a benzyl, a C$_1$-C$_4$-alkyl, a C$_1$-C$_4$-halogenoalkyl having 1 to 5 halogen atoms, a hydroxy-C$_1$-C$_4$-alkyl, a C$_2$-C$_6$-alkenyl, a C$_3$-C$_6$-cycloalkyl, a C$_1$-C$_4$-alkylthio-C$_1$-C$_4$-alkyl, a C$_1$-C$_4$-halogenoalkylthio-C$_1$-C$_4$-alkyl having 1 to 5 halogen atoms, a C$_1$-C$_4$-alkoxy-C$_1$-C$_4$-alkyl, a C$_1$-C$_4$-halogenoalkoxy-C$_1$-C$_4$-alkyl having 1 to 5 halogen atoms;
provided that R$^{44}$ and R$^{45}$ are not both a hydrogen atom.

Het represents a heterocycle of the general formula (Het-15)

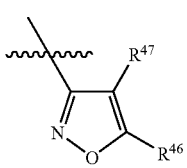

(Het-15)

in which:
R$^{46}$ may be a hydrogen atom, a halogen atom, a C-C$_4$-alkyl or a C$_1$-C$_4$-halogenoalkyl having 1 to 5 halogen atoms; and
R$^{47}$ may be a halogen atom, a C-C$_4$-alkyl or a C$_1$-C$_4$-halogenoalkyl having 1 to 5 halogen atoms.

Het represents a heterocycle of the general formula (Het-16)

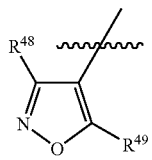
(Het-16)

in which $R^{48}$ and $R^{49}$ may be the same or different and may be a hydrogen atom, a halogen atom, a $C_1$-$C_4$-alkyl, a $C_1$-$C_4$-halogenoalkyl having 1 to 5 halogen atoms, a phenyl optionally substituted by a halogen atom or a $C_1$-$C_4$-alkyl, or a heterocyclyl optionally substituted by a halogen atom or a $C_1$-$C_4$-alkyl;

provided that $R^{48}$ and $R^{498}$ are not both a hydrogen atom.

Het represents a heterocycle of the general formula (Het-17)

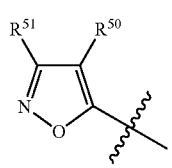
(Het-17)

in which
$R^{50}$ may be a halogen atom, a $C_1$-$C_4$-alkyl or a $C_1$-$C_4$-halogenoalkyl having 1 to 5 halogen atoms and
$R^{51}$ may be a halogen atom, a $C_1$-$C_4$-alkyl or a $C_1$-$C_4$-halogenoalkyl having 1 to 5 halogen atoms.

Het represents a heterocycle of the general formula (Het-18)

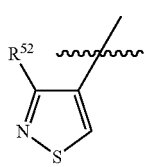
(Het-18)

in which $R^{52}$ may be a halogen atom, a $C_1$-$C_4$-alkyl or a $C_1$-$C_4$-halogenoalkyl having 1 to 5 halogen atoms.

Het represents a heterocycle of the general formula (Het-19)

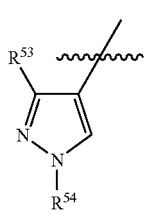
(Het-19)

in which:
$R^{53}$ may be a halogen atom, a $C_1$-$C_4$-alkyl or a $C_1$-$C_4$-halogenoalkyl having 1 to 5 halogen atoms; and
$R^{54}$ may be a hydrogen atom, a $C_1$-$C_4$-alkyl, a $C_1$-$C_4$-halogenoalkyl having 1 to 5 halogen atoms, or a phenyl optionally substituted by a halogen atom or a $C_1$-$C_4$-alkyl.

Het represents a heterocycle of the general formula (Het-20)

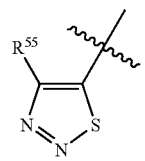
(Het-20)

in which $R^{55}$ may be a halogen atom, a $C_1$-$C_4$-alkyl or a $C_1$-$C_4$-halogenoalkyl having 1 to 5 halogen atoms.

Het may represent a heterocycle of the general formula (Het-21)

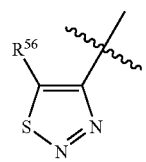
(Het-21)

in which $R^{56}$ may be a halogen atom, a $C_1$-$C_4$-alkyl or a $C_1$-$C_4$-halogenoalkyl having 1 to 5 halogen atoms.

According to the present invention, the nitrogen atom of the carboxamide moiety of the compound of formula (I) is substituted by $R^1$, $R^1$ being a hydrogen atom or a $C_3$-$C_7$-cycloalkyl. Preferably, the $C_3$-$C_7$-cycloalkyl is cyclopropyl.

According to the present invention, the first carbon atom of the alkyl chain of the compound of formula (I) is substituted by $R^2$, $R^2$ being as defined above. Preferably, the present invention also relates to N-alkyl-heterocyclyl carboxamide derivative of general formula (I) in which $R^2$ may be chosen as being a $C_1$-$C_3$ alkyl. More preferably, $R^2$ is a methyl group.

According to the present invention, the alkyl chain of the compound of formula (I) further comprises n carbon atoms, each of which being substituted by $R^3$, $R^3$ being as defined above. Preferably, the present invention also relates to N-alkyl-heterocyclyl carboxamide derivative of general formula (I) in which the different characteristics may be chosen alone or in combination as being:
as regards n, n is 3; and
as regards $R^3$, $R^3$ is a methyl group.

According to the present invention, the last carbon atom of the alkyl chain of the compound of formula (I) is substituted by $R^4$, $R^5$ and $R^6$, $R^4$, $R^5$ and $R^6$ being as defined above. Preferably, the present invention also relates to N-alkyl-heterocyclyl carboxamide derivative of general formula (I) in which $R^4$, $R^5$ and $R^6$ may be chosen, independently of each other as being a hydrogen atom or a methyl group.

According to the present invention, the alkyl chain of the compound of formula (I) contains from 2 to 4 carbon atoms, each of which is substituted by a substituent X which may the same or different. Preferably, the present invention relates to N-alkyl-heterocyclyl carboxamide derivative of general formula (I) in which X is chosen as being a hydrogen atom or a methyl group.

Preferably, the present invention also relates to N-alkyl-heterocyclyl carboxamide derivative of general formula (I-a)

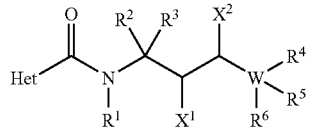
(I-a)

in which:

Het, $R^1$, $R^2$, $R^3$, $R^4$, $R^5$ and $R^6$ are as defined above; and $X^1$ and $X^2$ are chosen, independently of each other, as being a hydrogen atom or a methyl group.

Preferably, the present invention also relates to N-alkyl-heterocyclyl carboxamide derivative of general formula (I-b)

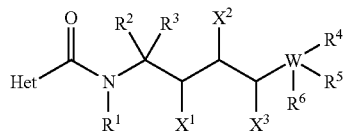
(I-b)

in which:

Het, $R^1$, $R^2$, $R^3$, $R^4$, $R^5$ and $R^6$ are as defined above; and $X^1$, $X^2$ and $X^3$ are chosen, independently of each other, as being a hydrogen atom or a methyl group.

Preferably, the present invention also relates to N-alkyl-heterocyclyl carboxamide derivative of general formula (I-c)

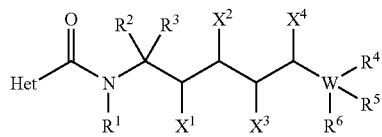
(I-c)

in which:

Het, $R^1$, $R^2$, $R^3$, $R^4$, $R^5$ and $R^6$ are as defined above; and $X^1$, $X^2$, $X^3$ and $X^4$ are chosen, independently of each other, as being a hydrogen atom or a methyl group.

The present invention also relates to a process for the preparation of the compound of general formula (I). Thus, according to a further aspect of the present invention there is provided a process for the preparation of compound of general formula (I) as defined above, which comprises reacting an alkyl-amine derivative of general formula (II) or one of its salt

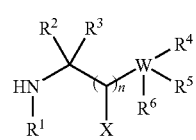
(II)

in which $R^1$, $R^2$, $R^3$, X, n, W, $R^4$, $R^5$ and $R^6$ are as defined above; with a carboxylic acid derivative of the general formula (III)

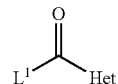
(III)

in which:

Het is as defined above; and $L^1$ is a leaving group chosen as being a halogen atom, a hydroxyl group, —$OR^{54}$, —$OCOR^{54}$, $R^{54}$ being a $C_1$-$C_6$ alkyl, a $C_1$-$C_6$ haloalkyl, a benzyl, 4-methoxybenzyl, pentafluorophenyl or a group of formula

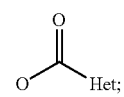

in the presence of a catalyst and, if $L^1$ is a hydroxyl group, in the presence of a condensing agent.

The process according to the present invention is conducted in the presence of a catalyst. Suitable catalyst may be chosen as being 4-dimethyl-aminopyridine, 1-hydroxy-benzotriazole or dimethylformamide.

In case $L^1$ is a hydroxy group, the process according to the present invention is conducted in the presence of condensing agent. Suitable condensing agent may be chosen as being acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl-chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5]triazin-2-yl)-4-methylmorpholinium chloride hydrate or bromo-tripyrrolidino-phosphonium-hexafluorophosphate.

When $R^1$ is a hydrogen atom, the above mentioned process for the preparation of compound of general formula (I) may optionally be completed by a further step according to the following reaction scheme:

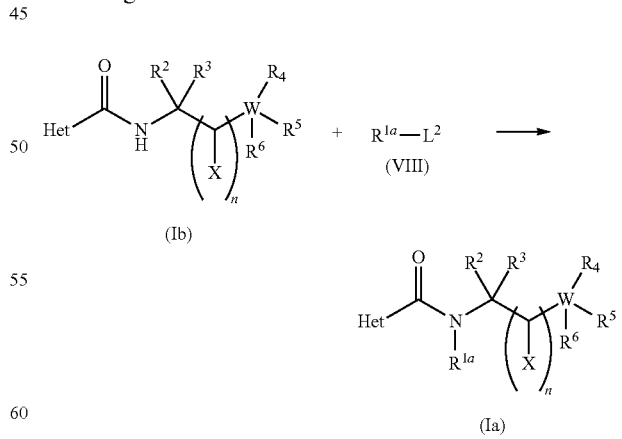

in which: $R^2$, $R^3$, X, n, W, $R^4$, $R^5$, $R^6$ and Het are as defined above;

$L^2$ is a leaving group chosen as being a halogen atom, a 4-methyl phenylsulfonyloxy or a methylsulfonyloxy; and $R^{1a}$ is a $C_1$-$C_6$-alkyl group or a $C_3$-$C_7$-cycloalkyl;

comprising the reaction of a compound of general formula (Ib) with a compound of general formula (VIII) to provide a compound of general formula (Ia).

Depending on the definition of $R^1$, $R^2$, $R^3$, X, n, $R^4$, $R^5$ and $R^6$, amine derivatives of general formula (II) may be prepared by different processes. One example (A) of such a process may be when:

$R^1$, $R^2$, X, n, W, $R^4$, $R^5$ and $R^6$ are as defined above; and $R^3$ is a hydrogen atom;

then, the amine derivative of general formula (II) may be prepared according to a process which comprises:

a first step according to reaction scheme A-1:

Scheme A-1

(IV)

(V)

in which $R^1$, $R^2$, X, n, W, $R^4$, $R^5$ and $R^6$ are as defined above;

comprising the reaction of a compound of general formula (IV) with an amine of formula $R^1$—$NH_2$ to provide an imine derivative of general formula (V);

a second step according to scheme A-2:

Scheme A-2

(V)　　(IIa)

in which $R^1$, $R^2$, X, n, W, $R^4$, $R^5$ and $R^6$ are as defined above;

comprising the reduction of an imine derivative of general formula (V) by hydrogenation or by an hydride donor, in the same or a different pot to provide an amine derivative of general formula (IIa) or one of its salt.

An other example (B) of such a process may be when:

$R^2$, $R^3$, X, n, W, $R^4$, $R^5$, $R^6$ are as defined above;

$R^1$ is a hydrogen atom then, the amine derivative of general formula (II) may be prepared according to a process which comprises:

a first step according to reaction scheme B-1:

Scheme B-1

(VI)　　(VII)

in which:

$R^2$, $R^3$, X, n, W, $R^4$, $R^5$ and $R^6$ are as defined above; and

U is a leaving group chosen as being a halogen atom, a $C_1$-$C_6$ alkylsulfonate or a $C_1$-$C_6$ haloalkylsulfonate;

comprising the nucleophilic substitution of a compound of general formula (VI) by a phthalimide salt to produce a compound of general formula (VII);

a second step according to reaction scheme B-2:

Scheme B-2

(VII)　　(IIb)

in which $R^2$, $R^3$, X, n, W, $R^4$, $R^5$, $R^6$ are as defined above;

comprising the de-protection of a compound of general formula (VII) by reacting it with hydrazine hydrate or a hydrazine salt to provide an amine derivative of general formula (IIb) or one of its salt;

The compound of general formula (II) used as an intermediate for the preparation of compound of general formula (I) is novel. Therefore, the present invention also relates to novel intermediate compound useful for the preparation of compound of general formula (I). Thus, according to the present invention, there is provided a compound of general formula (II)

(II)

in which $R^1$, $R^2$, $R^3$, X, n, W, $R^4$, $R^5$ and $R^6$ are as defined above The present invention also relates to a fungicidal composition comprising an effective amount of an active material of general formula (I). Thus, according to the present invention, there is provided a fungicidal composition comprising, as an active ingredient, an effective amount of a compound of general formula (I) as defined above and an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Optionally, additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds of the invention can also be mixed with one or more insecticides, fungicides, bactericides, attractant acaricides or pheromones or other compounds with biological activity. The mixtures thus obtained have a broadened spectrum of activity. The mixtures with other fungicides are particularly advantageous. Examples of suitable fungicide mixing partners may be selected in the following lists:

1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid;

2) a compound capable to inhibit the mitosis and cell division like benomyl, carbendazim, diethofencarb, fuberidazole, pencycuron, thiabendazole thiophanate-methyl, zoxamide;

3) a compound capable to inhibit the respiration for example
   as CI-respiration inhibitor like diflumetorim;
   as CII-respiration inhibitor like boscalid, carboxin, fenfuram, flutolanil, furametpyr, mepronil, oxycarboxine, penthiopyrad, thifluzamide;
   as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

4) a compound capable of to act as an uncoupler like dinocap, fluazinam;

5) a compound capable to inhibit ATP production like fentin acetate, fentin chloride, fentin hydroxide, silthiofam;

6) a compound capable to inhibit AA and protein biosynthesis like andoprim, blasticidin-S, cyprodinil, kasugamycin, kasugamycin hydrochloride hydrate, mepanipyrim, pyrimethanil;

7) a compound capable to inhibit the signal transduction like fenpiclonil, fludioxonil, quinoxyfen;

8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

10) a compound capable to inhibit cell wall synthesis like benthiavalicarb, bialaphos, dimethomorph, flumorph, iprovalicarb, polyoxins, polyoxorim, validamycin A;

11) a compound capable to inhibit melanine biosynthesis like carpropamid, diclocymet, fenoxanil, phtalide, pyroquilon, tricyclazole;

12) a compound capable to induce a host defense like acibenzolar-S-methyl, probenazole, tiadinil;

13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethyl-isoxazolidin-3-yl]pyridine, cis-1-(4-chlorophenyl)-2-(1H-1,2,4-triazole-1-yl)-cyclo heptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-alpha.-(methoxymethylene)-benzeneacetate, 4-Chloro-alpha-propynyloxy-N-[2-[3-methoxy-4-(2-propynyloxy) phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranone-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxy-benzamide, 2-[[[[1-[3 (1 Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The fungicidal compositions of the present invention can be used to curatively or preventively control the phytopathogenic fungi of crops. Thus, according to a further aspect of the present invention, there is provided a method for curatively or preventively controlling the phytopathogenic fungi of crops characterised in that a fungicidal composition as hereinbefore defined is applied to the seed, the plant and/or to the fruit of the plant or to the soil in which the plant is growing or in which it is desired to grow.

The composition as used against phytopathogenic fungi of crops comprises an effective and non-phytotoxic amount of an active material of general formula (I).

The expression "effective and non-phytotoxic amount" means an amount of composition according to the invention which is sufficient to control or destroy the to fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicidal composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of: cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

Among the diseases of plants or crops that can be controlled by the method according to the present invention, mention may be made of:

Powdery mildew diseases such as:
  Blumeria diseases, caused for example by Blumeria graminis;
  Podosphaera diseases, caused for example by Podosphaera leucotricha;
  Sphaerotheca diseases, caused for example by Sphaerotheca fuliginea;
  Uncinula diseases, caused for example by Uncinula necator;

Rust diseases such as:
  Gymnosporangium diseases, caused for example by Gymnosporangium sabinae;
  Hemileia diseases, caused for example by Hemileia vastatrix;
  Phakopsora diseases, caused for example by Phakopsora pachyrhizi or Phakopsora meibomiae;

Puccinia diseases, caused for example by *Puccinia recondita*;
Uromyces diseases, caused for example by *Uromyces appendiculatus*;
Oomycete diseases such as:
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;
Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporium cucumerinum*;
Cochliobolus diseases, caused for example by *Cochliobolus sativus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella arachidicola*; *Mycosphaerella fijiensis*;
Phaeosphaeria diseases, caused for example by *Phaeosphaeria nodorum*;
Pyrenophora diseases, caused for example by *Pyrenophora teres*;
Ramularia diseases, caused for example by *Ramularia collo-cygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incarnata*;
Venturia diseases, caused for example by *Venturia inaequalis*;
Root and stem diseases such as:
Corticium diseases, caused for example by *Corticium graminearum*;
Fusarium diseases, caused for example by *Fusarium oxysporum*;
Gaeumannomyces diseases, caused for example by *Gaeumannomyces graminis*;
Rhizoctonia diseases, caused for example by *Rhizoctonia solani*;
Tapesia diseases, caused for example by *Tapesia acuformis*;
Thielaviopsis diseases, caused for example by *Thielaviopsis basicola*;
Ear and panicle diseases such as:
Alternaria diseases, caused for example by *Alternaria* spp.;
Aspergillus diseases, caused for example by *Aspergillus flavus*;
Cladosporium diseases, caused for example by *Cladosporium* spp.;
Claviceps diseases, caused for example by *Claviceps purpurea*;
Fusarium diseases, caused for example by *Fusarium culmorum*;
Gibberella diseases, caused for example by *Gibberella zeae*;
Monographella diseases, caused for example by *Monographella nivalis*;
Smut and bunt diseases such as:
Sphacelotheca diseases, caused for example by *Sphacelotheca reiliana*;
Tilletia diseases, caused for example by *Tilletia caries*;
Urocystis diseases, caused for example by *Urocystis occulta*;
Ustilago diseases, caused for example by *Ustilago nuda*;
Fruit rot and mould diseases such as:
Aspergillus diseases, caused for example by *Aspergillus flavus*;
Botrytis diseases, caused for example by *Botrytis cinerea*;
Penicillium diseases, caused for example by *Penicillium expansum*;
Sclerotinia diseases, caused for example by *Sclerotinia sclerotiorum*;
Verticilium diseases, caused for example by *Verticilium alboatrum*;
Seed and soilborne decay, mould, wilt, rot and damping-off diseases:
Fusarium diseases, caused for example by *Fusarium culmorum*;
Phytophthora diseases, caused for example by *Phytophthora cactorum*;
Pythium diseases, caused for example by *Pythium ultimum*;
Rhizoctonia diseases, caused for example by *Rhizoctonia solani*;
Sclerotium diseases, caused for example by *Sclerotium rolfsii*;
Microdochium diseases, caused for example by *Microdochium nivale*;
Canker, broom and dieback diseases such as:
Nectria diseases, caused for example by *Nectria galligena*;
Blight diseases such as:
Monilinia diseases, caused for example by *Monilinia laxa*;
Leaf blister or leaf curl diseases such as:
Taphrina diseases, caused for example by *Taphrina deformans*;
Decline diseases of wooden plants such as:
Esca diseases, caused for example by *Phaemoniella clamydospora*;
Diseases of flowers and Seeds such as:
Botrytis diseases, caused for example by *Botrytis cinerea*;
Diseases of tubers such as:
Rhizoctonia diseases, caused for example by *Rhizoctonia solani*.

The fungicide composition according to the present invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. The dose of active substance applied is generally and advantageously between 2 and 200 g per 100 kg of seed, preferably between 3 and 150 g per 100 kg of seed in the case of seed treatment. It is clearly understood that the doses indicated above are given as illustrative examples of the invention. A person skilled in the art will know how to adapt the application doses according to the nature of the crop to be treated.

limiting manner examples of fungicidal compounds according to the present invention. In the following Examples, M+1 (or M−1) means the molecular ion peak, plus or minus 1 a.m.u. (atomic mass units) respectively, as observed in mass spectroscopy.

TABLE 1

| Compound | $R^1$ | $R^2$ | $R^3$ | n | $X^1$ | $X^2$ | $X^3$ | W | $R^4$ | $R^5$ | $R^6$ | [M + 1] |
|---|---|---|---|---|---|---|---|---|---|---|---|---|
| 1-1 | H | Me | H  | 2 | H  | H  | —  | C | H | Me | Me | 349 |
| 1-2 | H | Me | H  | 3 | H  | H  | H  | C | H | Me | Me | 363 |
| 1-3 | H | Me | Me | 3 | H  | H  | H  | C | H | Me | Me | 377 |

TABLE 2

| Compound | $R^1$ | $R^2$ | $R^3$ | n | $X^1$ | $X^2$ | $X^3$ | W | $R^4$ | $R^5$ | $R^6$ | [M + 1] |
|---|---|---|---|---|---|---|---|---|---|---|---|---|
| 2-1 | H | Me | H | 2 | H | H | — | C | H | Me | Me | 291 |
| 2-2 | H | Me | H | 3 | H | H | H | C | H | Me | Me | 305 |
| 2-3 | H | Me | Me | 3 | H | H | H | C | H | Me | Me | 319 |
| 2-4 | Cyclopropyl | Me | H | 3 | H | Me | H | Si | Me | Me | Me | 389 |
| 2-5 | H | Me | H | 3 | Me | Me | H | Si | Me | Me | Me | 363 |
| 2-6 | H | Me | H | 3 | H | Me | H | Si | Me | Me | Me | 349 |

The fungicidal composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The compositions according to the present invention may also be used for the preparation of composition useful to curatively or preventively treat human and animal fungal diseases such as, for example, mycoses, dermatoses, *trichophyton* diseases and candidiases or diseases caused by *Aspergillus* spp., for example *Aspergillus fumigatus*.

The aspects of the present invention will now be illustrated with reference to the following tables of compounds and examples. The following Tables A to V illustrate in a non-

TABLE 3

| Compound | $R^1$ | $R^2$ | $R^3$ | n | $X^1$ | $X^2$ | $X^3$ | W | $R^4$ | $R^5$ | $R^6$ | [M + 1] |
|---|---|---|---|---|---|---|---|---|---|---|---|---|
| 3-1 | H | Me | H  | 2 | H  | H  | —  | C  | H  | Me | Me | 352 |
| 3-2 | H | Me | H  | 3 | H  | H  | H  | C  | H  | Me | Me | 366 |
| 3-3 | H | Me | H  | 3 | Me | Me | H  | Si | Me | Me | Me | 410 |
| 3-4 | H | Me | Me | 3 | H  | H  | H  | C  | H  | Me | Me | 380 |
| 3-5 | H | Me | H  | 3 | H  | Me | H  | Si | Me | Me | Me | 410 |

TABLE 4

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 4-1 | H | Me | H | 2 | H | H | — | C | H | Me | Me | 292 |
| 4-2 | H | Me | H | 3 | H | H | H | C | H | H | Me | 292 |
| 4-3 | H | Me | H | 3 | H | H | H | Si | Me | Me | Me | 336 |
| 4-4 | H | Me | H | 3 | H | Me | H | C | Me | Me | Me | 334 |
| 4-5 | H | Me | H | 3 | H | Me | H | Si | Me | Me | Me | 350 |
| 4-6 | H | Me | H | 3 | Me | Me | H | Si | Me | Me | Me | 364 |
| 4-7 | H | Me | Me | 3 | H | H | H | C | H | Me | Me | 320 |
| 4-8 | Cyclopropyl | Me | H | 3 | H | Me | H | Si | Me | Me | Me | 390 |
| 4-9 | H | (R)-Me | H | 3 | H | (R)-Me | H | C | Me | Me | Me | 334 |
| 4-10 | H | (R)-Me | H | 3 | H | (S)-Me | H | C | Me | Me | Me | 334 |
| 4-11 | H | (S)-Me | H | 3 | H | (S)-Me | H | C | Me | Me | Me | 334 |
| 4-12 | H | (S)-Me | H | 3 | H | (R)-Me | H | C | Me | Me | Me | 334 |

TABLE 5

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 5-1 | H | Me | H | 2 | H | H | — | C | H | Me | Me | 274 |
| 5-2 | H | Me | H | 3 | H | H | H | C | H | H | Me | 274 |
| 5-3 | H | Me | H | 3 | H | Me | H | C | Me | Me | Me | 316 |
| 5-4 | H | Me | H | 3 | H | Me | H | Si | Me | Me | Me | 332 |
| 5-5 | H | Me | H | 3 | Me | Me | H | Si | Me | Me | Me | 346 |
| 5-6 | H | Me | Me | 3 | H | H | H | C | H | Me | Me | 302 |
| 5-7 | Cyclopropyl | Me | H | 3 | H | Me | H | Si | Me | Me | Me | 372 |

TABLE 6

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 6-1 | H | Me | H | 3 | Me | Me | H | Si | Me | Me | Me | 340 |

TABLE 7

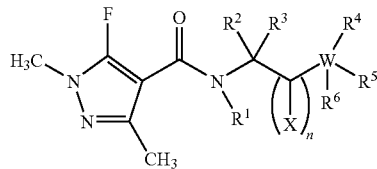

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 7-1 | H | Me | H | 2 | H | H | — | C | H | Me | Me | 256 |
| 7-2 | H | Me | H | 3 | H | Me | H | C | Me | Me | Me | 298 |
| 7-3 | H | Me | H | 3 | H | Me | H | Si | Me | Me | Me | 314 |
| 7-4 | H | Me | H | 3 | Me | Me | H | Si | Me | Me | Me | 328 |
| 7-5 | H | Me | Me | 3 | H | H | H | C | H | Me | Me | 284 |
| 7-6 | Cyclopropyl | Me | H | 3 | H | Me | H | Si | Me | Me | Me | 354 |

TABLE 8

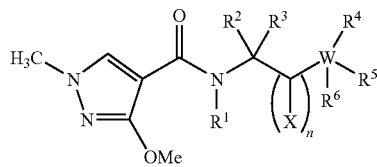

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 8-1 | H | Me | H | 3 | H | Me | H | C | Me | Me | Me | 296 |
| 8-2 | H | Me | H | 3 | H | Me | H | Si | Me | Me | Me | 312 |
| 8-3 | H | Me | H | 3 | Me | Me | H | Si | Me | Me | Me | 326 |
| 8-4 | Cyclopropyl | Me | H | 3 | H | Me | H | Si | Me | Me | Me | 352 |

TABLE 9

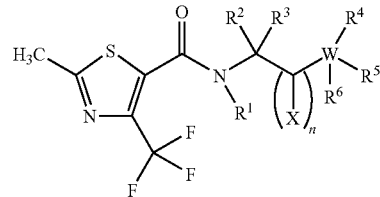

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 9-1 | H | Me | H | 2 | H | H | — | C | H | Me | Me | 309 |
| 9-2 | H | Me | H | 3 | H | H | H | C | H | H | Me | 309 |
| 9-3 | H | Me | H | 3 | H | Me | H | Si | Me | Me | Me | 367 |
| 9-4 | H | Me | H | 3 | Me | Me | H | Si | Me | Me | Me | 381 |
| 9-5 | H | Me | Me | 3 | H | H | H | C | H | Me | Me | 337 |
| 9-6 | Cyclopropyl | Me | H | 3 | H | Me | H | Si | Me | Me | Me | 407 |
| 9-7 | H | Me | H | 3 | H | Me | H | C | Me | Me | Me | 6.03 (d, 1H) 4.14 (m, 1H) 2.71 (m, 3H) 1.58 (m, 1H) 1.40 (m, 2H) 1.24 (m, 1H) 1.21 (d, 3H) 1.08 (dd, 1H) 0.97 (d, 3H) 0.89 (s, 9H) |

TABLE 10

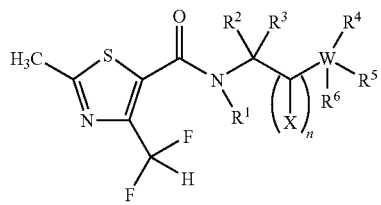

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 10-1 | H | Me | H | 2 | H | H | — | C | H | Me | Me | 291 |
| 10-2 | H | Me | H | 3 | H | H | H | C | H | H | Me | 291 |
| 10-3 | H | Me | H | 3 | H | H | H | Si | Me | Me | Me | 335 |
| 10-4 | H | Me | H | 3 | H | Me | H | C | Me | Me | Me | 333 |
| 10-5 | H | Me | H | 3 | H | Me | H | Si | Me | Me | Me | 349 |
| 10-6 | H | Me | H | 3 | Me | H | H | Si | Me | Me | Me | 363 |
| 10-7 | H | Me | Me | 3 | H | H | H | C | H | Me | Me | 319 |
| 10-8 | Cyclopropyl | Me | H | 3 | H | Me | H | Si | Me | Me | Me | 389 |

TABLE 11

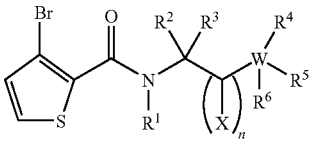

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 11-1 | H | Me | H | 2 | H | H | — | C | H | Me | Me | 304 |
| 11-2 | H | Me | H | 3 | H | H | H | C | H | Me | Me | 318 |
| 11-3 | H | Me | H | 3 | Me | H | C | Me | Me | Me |  | 346 |
| 11-4 | H | Me | Me | 3 | H | H | H | C | H | Me | Me | 332 |
| 11-5 | H | Me | H | 3 | Me | Me | H | Si | Me | Me | Me | 377 |
| 11-6 | H | Me | H | 3 | H | Me | H | Si | Me | Me | Me | 363 |

TABLE 12

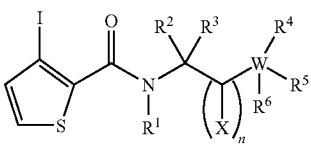

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 12-1 | H | Me | H | 2 | H | H | — | C | H | Me | Me | 352 |
| 12-2 | H | Me | H | 3 | H | H | H | C | H | Me | Me | 366 |
| 12-3 | H | Me | Me | 3 | H | H | H | C | H | Me | Me | 380 |

TABLE 13

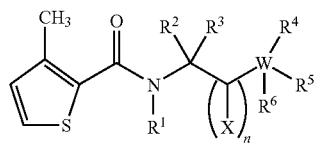

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 13-1 | H | Me | H | 2 | H | H | — | C | H | Me | Me | 240 |
| 13-2 | H | Me | H | 3 | H | H | H | C | H | Me | Me | 254 |
| 13-3 | H | Me | H | 3 | Me | Me | H | Si | Me | Me | Me | 312 |
| 13-4 | H | Me | Me | 3 | H | H | H | C | H | Me | Me | 268 |
| 13-5 | H | Me | H | 3 | Me | Me | H | Si | Me | Me | Me | 312 |

TABLE 14

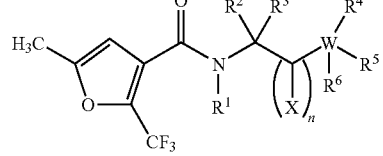

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 14-1 | H | Me | H | 2 | H | H | — | C | H | Me | Me | 292 |
| 14-2 | H | Me | H | 3 | H | H | H | C | H | Me | Me | 306 |

TABLE 14-continued

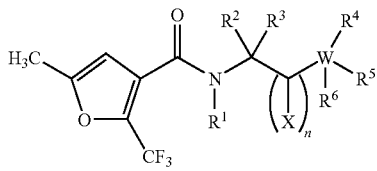

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 14-3 | Cyclopropyl | Me | H | 3 | H | Me | H | Si | Me | Me | Me | 390 |
| 14-4 | H | Me | H | 3 | Me | Me | H | Si | Me | Me | Me | 364 |

TABLE 15

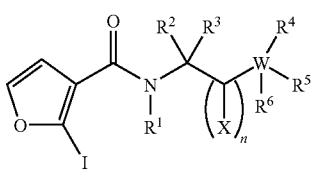

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 15-1 | H | Me | H | 2 | H | H | — | C | H | Me | Me | 336 |
| 15-2 | H | Me | H | 3 | H | H | H | C | H | Me | Me | 350 |
| 15-3 | H | Me | H | 3 | Me | Me | H | Si | Me | Me | Me | 406 |
| 15-4 | H | Me | Me | 3 | H | H | H | C | H | Me | Me | 364 |

TABLE 16

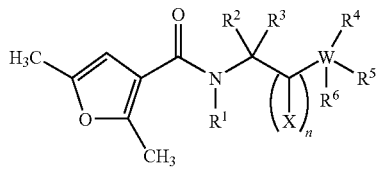

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 16-1 | H | Me | H | 2 | H | H | — | C | H | Me | Me | 238 |
| 16-2 | H | Me | H | 3 | H | H | H | C | H | Me | Me | 252 |
| 16-3 | H | Me | H | 3 | Me | Me | H | Si | Me | Me | Me | 310 |
| 16-4 | H | Me | H | 3 | Me | Me | H | Si | Me | Me | Me | 310 |

TABLE 17

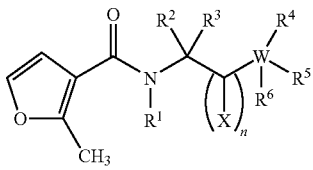

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 17-1 | H | Me | H | 2 | H | H | — | C | H | Me | Me | 224 |
| 17-2 | H | Me | H | 3 | H | H | H | C | H | Me | Me | 238 |
| 17-3 | H | Me | H | 3 | H | Me | H | C | Me | Me | Me | 266 |
| 17-4 | H | Me | H | 3 | Me | Me | H | Si | Me | Me | Me | 296 |
| 17-5 | H | Me | H | 3 | Me | Me | H | Si | Me | Me | Me | 296 |

TABLE 18

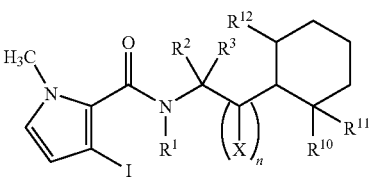

TABLE 19

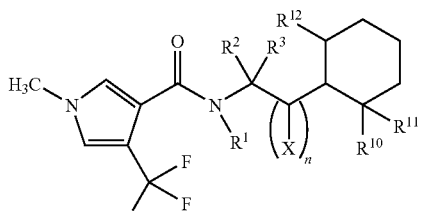

| Compound | R¹ | R² | R³ | n | X¹ | X² | R¹⁰ | R¹¹ | R¹² | [M + 1] |
|---|---|---|---|---|---|---|---|---|---|---|
| 19-1 | H | Me | H | 1 | H | — | H | H | H | 317 |

TABLE 20

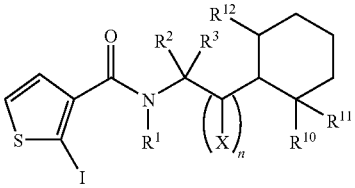

| Compound | R¹ | R² | R³ | n | X¹ | X² | R¹⁰ | R¹¹ | R¹² | [M + 1] |
|---|---|---|---|---|---|---|---|---|---|---|
| 20-1 | H | Me | H | 1 | H | — | H | H | H | 378 |

TABLE 21

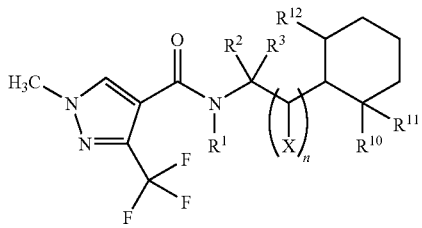

| Compound | R¹ | R² | R³ | n | X¹ | X² | R¹⁰ | R¹¹ | R¹² | [M + 1] |
|---|---|---|---|---|---|---|---|---|---|---|
| 21-1 | H | Me | H | 1 | H | — | H | H | H | 318 |
| 21-2 | H | Me | H | 2 | H | H | H | H | H | 332 |
| 21-3 | H | Me | H | 2 | H | H | Me | Me | Me | 388 |

TABLE 22

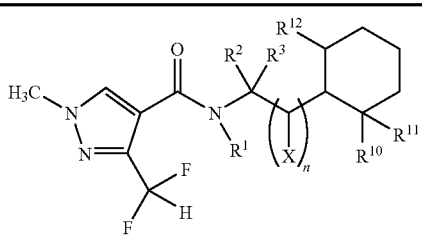

| Compound | R¹ | R² | R³ | n | X¹ | X² | R¹⁰ | R¹¹ | R¹² | [M + 1] |
|---|---|---|---|---|---|---|---|---|---|---|
| 22-1 | H | Me | H | 1 | H | — | H | H | H | 300 |
| 22-2 | H | Me | H | 2 | H | H | H | H | H | 314 |
| 22-3 | H | Me | H | 2 | H | H | Me | Me | Me | 370 |

TABLE 23

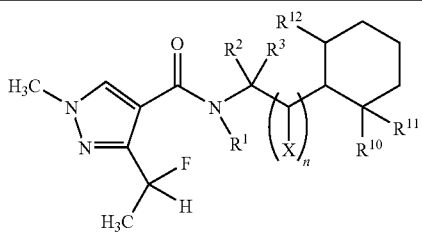

| Compound | R¹ | R² | R³ | n | X¹ | X² | R¹⁰ | R¹¹ | R¹² | [M + 1] |
|---|---|---|---|---|---|---|---|---|---|---|
| 23-1 | H | Me | H | 1 | H | — | H | H | H | 296 |

TABLE 24

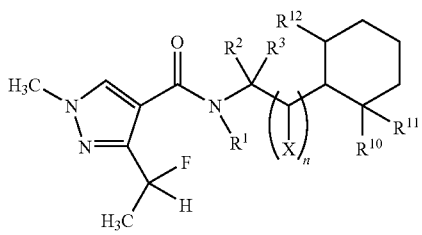

| Compound | R¹ | R² | R³ | n | X¹ | X² | R¹⁰ | R¹¹ | R¹² | [M + 1] |
|---|---|---|---|---|---|---|---|---|---|---|
| 24-1 | H | Me | H | 1 | H | — | H | H | H | 282 |
| 24-2 | H | Me | H | 2 | H | H | Me | Me | Me | 352 |

TABLE 25

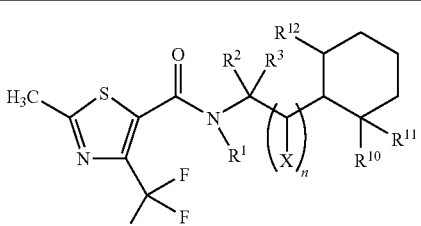

| Compound | R¹ | R² | R³ | n | X¹ | X² | R¹⁰ | R¹¹ | R¹² | [M + 1] |
|---|---|---|---|---|---|---|---|---|---|---|
| 25-1 | H | Me | H | 1 | H | — | H | H | H | 335 |
| 25-2 | H | Me | H | 2 | H | H | H | H | H | 349 |
| 25-3 | H | Me | H | 2 | H | H | Me | Me | Me | 405 |

TABLE 26

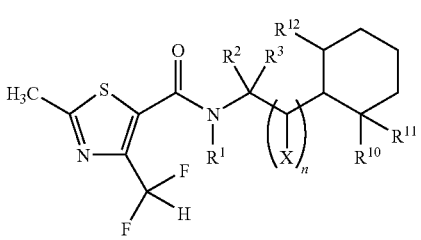

TABLE 27

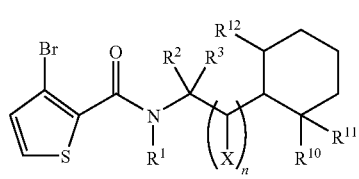

| Compound | R¹ | R² | R³ | n | X¹ | X² | R¹⁰ | R¹¹ | R¹² | [M + 1] |
|---|---|---|---|---|---|---|---|---|---|---|
| 27-1 | H | Me | H | 1 | H | — | H | H | H | 330 |

TABLE 28

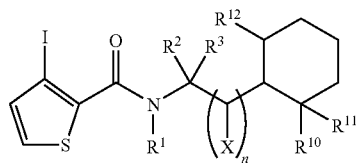

| Compound | R¹ | R² | R³ | n | X¹ | X² | R¹⁰ | R¹¹ | R¹² | [M + 1] |
|---|---|---|---|---|---|---|---|---|---|---|
| 28-1 | H | Me | H | 1 | H | — | H | H | H | 378 |
| 28-2 | H | Me | H | 2 | H | H | Me | Me | Me | 448 |

TABLE 29

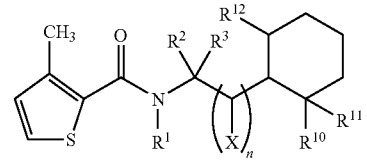

| Compound | R¹ | R² | R³ | n | X¹ | X² | R¹⁰ | R¹¹ | R¹² | [M + 1] |
|---|---|---|---|---|---|---|---|---|---|---|
| 29-1 | H | Me | H | 1 | H | — | H | H | H | 266 |
| 29-2 | H | Me | H | 2 | H | H | Me | Me | Me | 336 |

TABLE 30

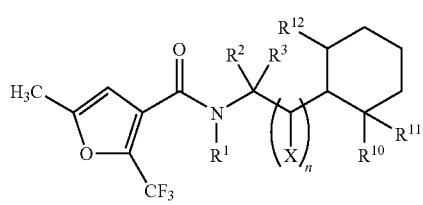

| Compound | R¹ | R² | R³ | n | X¹ | X² | R¹⁰ | R¹¹ | R¹² | [M + 1] |
|---|---|---|---|---|---|---|---|---|---|---|
| 30-1 | H | Me | H | 1 | H | — | H | H | H | 318 |
| 30-2 | H | Me | H | 2 | H | H | Me | Me | Me | 388 |

TABLE 31

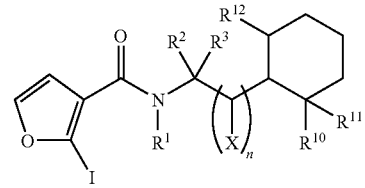

TABLE 32

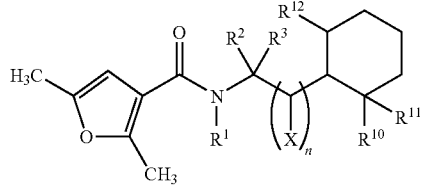

| Compound | R¹ | R² | R³ | n | X¹ | X² | R¹⁰ | R¹¹ | R¹² | [M + 1] |
|---|---|---|---|---|---|---|---|---|---|---|
| 32-1 | H | Me | H | 1 | H | — | H | H | H | 264 |
| 32-2 | H | Me | H | 2 | H | H | Me | Me | Me | 334 |

TABLE 33

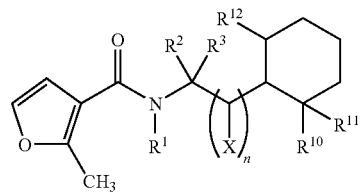

| Compound | R¹ | R² | R³ | n | X¹ | X² | R¹⁰ | R¹¹ | R¹² | [M + 1] |
|---|---|---|---|---|---|---|---|---|---|---|
| 33-1 | H | Me | H | 1 | H | — | H | H | H | 250 |
| 33-2 | H | Me | H | 2 | H | H | Me | Me | Me | 320 |

TABLE 34

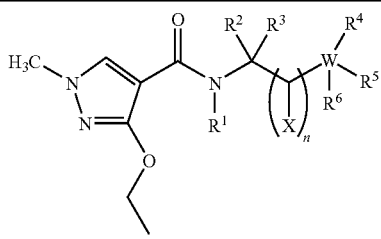

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 34-1 | H | Me | H | 3 | Me | Me | H | Si | Me | Me | Me | 340 |
| 34-2 | H | Me | H | 3 | H | Me | H | Si | Me | Me | Me | 326 |

TABLE 35

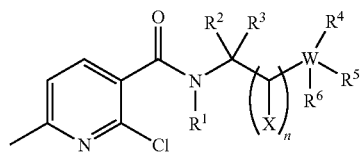

| Compound | R¹ | R² | R³ | n | X¹ | X² | X³ | W | R⁴ | R⁵ | R⁶ | [M + 1] |
|---|---|---|---|---|---|---|---|---|---|---|---|---|
| 35-1 | H | Me | H | 3 | Me | Me | H | Si | Me | Me | Me | 341 |
| 35-2 | H | Me | H | 3 | H | Me | H | Si | Me | Me | Me | 327 |

EXAMPLES OF PROCESS FOR THE PREPARATION OF THE COMPOUND OF GENERAL FORMULA (I)

Example 1

Preparation of N-[1,3-dimethyl-4-(trimethylsilyl)butyl]-5-fluoro-1,3-dimethyl-1H-pyrazole-4-carboxamide (Compound 7-3)

Preparation of 4-methyl-5-(trimethylsilyl)pentan-2-one

A solution of 8.00 g pent-3-en-2-one in 50 mL dry diethyl ether was dropped to a solution of 73.5 mL of chloro[(trimethylsilyl)methyl]magnesium (1.0M in diethyl ether) and 955 mg of CuBr at −5° C. under Argon. The mixture was stirred for 1 hour at room temperature. An aqueous work-up followed by silica gel chromatography yielded 5.20 g (43%) of a colourless oil.

[M+1]=173.

Preparation of 4-methyl-5-(trimethylsilyl)pentan-2-amine hydrochloride

A solution of 7.4 g 4-methyl-5-(trimethylsilyl)pentan-2-one, 29.8 g ammonium acetate, and 5 g molecular sieve 3 Å in 500 mL Methanol was stirred for 4 hours at room temperature. 4.86 g sodium cyanoborohydride was added. The reaction was completed over night at room temperature. The crude reaction mixture was evaporated. Extraction with diethyl ether, basic aqueous treatment and evaporation yielded 2.20 g (26%) of a colourless solid.

[M-HCl+1]=174.

Preparation of N-[1,3-dimethyl-4-(trimethylsilyl)butyl]-5-fluoro-1,3-dimethyl-M-pyrazole-4-carboxamide 91.6 mg of 5-fluoro-1,3-dimethyl-1H-pyrazole-4-carbonyl chloride was added to a solution of 173 mg 4-methyl-5-(trimethylsilyl)pentan-2-amine and 71.7 mg of potassium carbonate in 3 mL methylene chloride. The reaction mixture was stirred 2 hours at room temperature. Aqueous work-up, extraction with ethyl acetate and silica gel chromatography yielded 115 mg (67%) of a colourless oil.

[M+1]=314.

Example 2

Preparation of N-(3-cyclohexyl-1-methylpropyl)-3-(difluoromethyl)-1-methyl-1H-pyrazole-4-carboxamide (Compound 22-2)

Preparation of 3-cyclohexyl-1-methylpropyl methanesulfonate

A solution of 3.53 g methanesulfonyl chloride in 100 mL methylene chloride was added to a solution of 4.38 g 4-cyclohexylbutan-2-ol in 200 mL methylene chloride. The reaction mixture was stirred over night. Aqueous work-up yielded 7.06 g (96%) of a colourless oil.

Preparation of 2-(3-cyclohexyl-1-methylpropyl)-1H-isoindole-1,3(2H)-dione

A solution of 7.00 g 3-cyclohexyl-1-methylpropyl methanesulfonate in 20 mL DMF was added to a solution of 5.14 g phthalimide and 7.43 g of potassium carbonate in 50 mL DMF at room temperature. The reaction mixture was stirred at 80° C. over night. Aqueous work-up followed by silica gel filtration yielded 4.95 g (58%) of a colourless oil.

[M+1]=286.

Preparation of 4-cyclohexylbutan-2-amine

A solution of 4.60 g 2-(3-cyclohexyl-1-methylpropyl)-1H-iso indole-1,3(2H)-dione and 7.26 g of hydrazine hydrate in 60 mL ethanol was heated to 70° C. The white precipitation was filtered off after cooling to room temperature. The mixture was washed with water and evaporated. 920 mg (37%) of a colourless oil were obtained.

Preparation of N-(3-cyclohexyl-1-methylpropyl)-3-(difluoromethyl)-1-methyl-M-pyrazole-4-carboxamide A solution of 489 mg PS DCC [N-Cyclohexylcarbodiimide, N'-methyl polystyrene], 90.7 mg 3-(difluoromethyl)-1-methyl-1H-pyrazole-4-carboxylic acid, 69.6 mg 1-hydroxybenzotriazole (HOBT) in 3.2 mL acetonitrile was heated for 5 min to 100° C. in the microwave oven. After cooling the reaction mixture 200 mg of Amberlist A21 were added and the mixture was heated again to 100° C. in the microwave oven. The cold reaction mixture was filtered, the resin was washed with methylene chloride. Silica gel chromatography yielded 89 mg (52%) of a brownish oil.

[M+1]=314.

Example 3

Preparation of 4-(difluoromethyl)-2-methyl-N-[1-methyl-4-(trimethylsilyl)butyl]-1,3-thiazole-5-carboxamide (Compound 10-3)

A solution of 133 mg of 4-(difluoromethyl)-2-methyl-1,3-thiazole-5-carboxylic acid, 110 mg 5-(trimethylsilyl)pentan-2-amine, 354 mg of PyBroP [bromo-tris-pyrrolidino-phosphonium hexafluorophosphate], and 142 mg N,N'-diisopropylamine in 10 mL acetonitrile was stirred over night at room temperature. Aqueous work-up [extraction with 1.0M NaOH], and silica gel chromatography yielded 130 mg (53%) of a colourless oil.

[M+1]=335.

EXAMPLES OF BIOLOGICAL ACTIVITY OF THE COMPOUND OF GENERAL FORMULA (I)

Example A

In Vivo Test on *Alternaria brassicae* (Leaf Spot of Crucifers)

The active ingredient tested is prepared by homogenisation in DMSO (5% of the final volume), acetone (10% of the final volume) and tween 80 10% (5 μl/mg active ingredient).

Radish plants (Pernot variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material.

After 24 hours, the plants are contaminated by spraying them with an aqueous suspension of *Alternaria brassicae* spores (40,000 spores per cm$^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants.

Under these conditions, good (at least 70%) or total protection is observed at a dose of 500 ppm with the following compounds: 1-2, 2-2, 2-5, 3-2, 3-5, 4-3, 4-4, 4-5, 4-6, 5-4, 5-5, 5-7, 6-1, 7-1, 7-3, 7-4, 7-6, 9-3, 10-3, 10-4, 5, 10-6, 10-8, 11-1, 11-2, 12-2, 13-1, 13-3, 13-5, 15-2, 15-3, 16-4, 19-1, 20-1, 21-1, 21-2, 22-2, 22-3, 23-1, 24-1, 24-2, 25-1, 25-3, 26-2, 27-1, 28-2, 30-1, 30-2, 31-1, 32-1 and 33-2.

Under these conditions, 4-dichloro-N-octylisothiazol-5-carboxamide disclosed in the U.S. Pat. No. 5,240,951 (see compound 23) did not show any activity against *Alternaria brassicae*.

Example B

In Vivo Test on *Botrytis cinerea* (Cucumber Grey Mould)

The active ingredient tested is prepared by homogenisation in DMSO (5% of the final volume), acetone (10% of the final volume) and tween 80 10% (5 µl/mg active ingredient).

Cucumber plants (Marketer variety) in starter cups, sown on a 50/50 peat soil-pozzolana substrate and grown at 18-20° C., are treated at the cotyledon Z11 stage by spraying with the aqueous suspension described above. Plants, used as controls, are treated with an aqueous solution not containing the active material.

After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatin
50 g/L of cane sugar
2 g/L of NH4NO3
1 g/L of KH2PO4

The contaminated cucumber plants are settled for 5/7 days in a climatic room at 15-11° C. (day/night) and at 80% relative humidity.

Grading is carried out 5/7 days after the contamination, in comparison with the control plants. Under these conditions, good (at least 70%) or total protection is observed:

at a dose of 500 ppm with the following compounds: 2-1, 2-2, 3-2, 4-3, 4-4, 4-5, 4-7, 4-11, 5-4, 5-5, 5-6, 5-7, 7-1, 7-2, 7-5, 7-6, 9-3, 10-3, 10-4, 10-5, 11-2, 12-2, 13-2, 15-1, 15-2, 18-1, 19-1, 20-1, 21-1, 21-2, 22-2, 24-1, 25-2, 26-2, 27-1, 28-1, 29-1, 30-1, 31-1, 33-1 and 33-2; and at a dose of 250 ppm for the following compound: 2-6.

Under these conditions, N-isopropyl-4-methyl-1,2,3-thiadiazole-5-carboxamide disclosed in the International Patent Application WO 96/29871 (see compound 1-89), N-sec-butyl-2,5-dimethyl-3-furamide disclosed in GB patent application GB 1387652 (see compound 3) and 4-dichloro-N-octyl-isothiazole-5-carboxamide disclosed in the U.S. Pat. No. 5,240,951 (see compound 23) did not show any activity against *Botrytis cinerea*.

Example C

In Vivo Test on *Pyrenophora teres* (Barley Net Blotch)

The active ingredient tested is prepared by homogenisation in DMSO (5% of the final volume), acetone (10% of the final volume) and tween 80 10% (5 µl/mg active ingredient).

Barley plants (Express variety) in starter cups, sown on a 50/50 peat soil-pozzolana substrate and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) or total protection is observed:

at a dose of 500 ppm with the following compounds: 2-1, 2-2, 2-4, 2-5, 3-1, 3-2, 3-5, 4-5, 4-6, 4-8, 4-12, 5-4, 5-5, 5-7, 7-1, 7-2, 7-3, 7-4, 7-6, 8-4, 9-3, 9-4, 10-5, 10-6, 10-8, 11-5, 12-2, 14-4, 15-2, 16-4, 17-5, 19-1, 21-2, 21-3, 22-2, 22-3, 24-1, 24-2, 25-2, 25-3, 26-2, 26-3, 27-1, 28-2, 29-2, 30-1, 30-2, 31-1, 32-1, 33-1, 33-2 and 35-1, at a dose of 330 ppm for the following compound: 11-3;

at a dose of 250 ppm for the following compound: 2-6; and at a dose of 500 g/ha with the following compounds: 4-3, 4-4, 10-3, 10-4, 21-1, 22-1, 25-1 and 26-1.

Under these conditions, N-sec-butyl-2,5-dimethyl-3-furamide disclosed in GB patent application GB1387652 (see compound 3) did not show any activity against *Pyrenophora teres*.

Example D

In Vivo Test on *Sphaerotheca fuliginea* (Powdery Mildew)

The active ingredient tested is prepared by homogenisation in DMSO (5% of the final volume), acetone (10% of the final volume) and tween 80 10% (5 µl/mg active ingredient).

Gherkin plants (Vert petit de Paris variety) in starter cups, sown on a 50/50 peat soil-pozzolana substrate and grown at 20° C./23° C., are treated at cotyledon Z11 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gerkhin plants are incubated at about 20° C./25° C. and at 60/70% relative humidity.

Grading (% of efficacy) is carried out 21 days after the contamination, in comparison with the control plants. Under these conditions, good (at least 70%) or total protection is observed:

at a dose of 500 ppm with the following compounds: 2-1, 2-4, 2-5, 3-1, 3-3, 3-5, 4-3, 4-4, 4-5, 4-6, 4-8, 4-11, 4-12, 5-4, 5-5, 5-6, 5-7, 7-2, 7-3, 7-4, 7-5, 7-6, 8-4, 9-3, 10-3, 10-4, 10-5, 10-6, 13-3, 13-5, 14-4, 15-3, 21-1, 21-2, 21-3, 22-1, 22-2, 22-3, 24-2, 25-1, 25-2, 25-3, 26-1, 26-2, 26-3, 28-2, 29-2, 30-2, 33-1 and 33-2; and at a dose of 250 pmm for the following compound: 2-6.

Under these conditions, N-isopropyl-4-methyl-1,2,3-thiadiazole-5-carboxamide disclosed in the International Patent Application WO 96/29871 (see compound 1-89) and N-sec-butyl-2,5-dimethyl-3-furamide disclosed in GB patent application GB 1387652 (see compound 3) did not show any activity against *Sphaerotheca fuliginea*.

The invention claimed is:

1. A compound of formula (I)

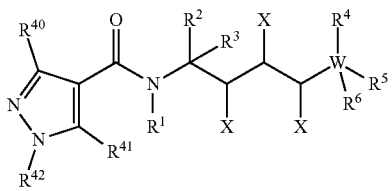

in which:
- $R^{40}$ is selected from the group consisting of a hydrogen atom, a halogen atom, a cyano group, a nitro group, a $C_1$-$C_4$-alkyl, a $C_1$-$C_4$-halogenoalkyl having 1 to 5 halogen atoms, a $C_3$-$C_6$-cycloalkyl, a $C_1$-$C_4$-alkoxy, a $C_1$-$C_4$-halogenoalkoxy having 1 to 5 halogen atoms, a $C_1$-$C_4$-alkylthio, a $C_1$-$C_4$-halogenoalkylthio having 1 to 5 halogen atoms, an aminocarbonyl, and an aminocarbonyl-$C_1$-$C_4$-alkyl;
- $R^{41}$ is selected from the group consisting of a hydrogen atom, a halogen atom, a cyano group, a $C_1$-$C_4$-alkyl, a $C_1$-$C_4$-alkoxy, a $C_1$-$C_4$-halogenoalkoxy having 1 to 5 halogen atoms, and a $C_1$-$C_4$-alkylthio; and
- $R^{42}$ is selected from the group consisting of a hydrogen atom, a $C_1$-$C_4$-alkyl, a $C_1$-$C_4$-halogenoalkyl having 1 to 5 halogen atoms, a hydroxy-$C_1$-$C_4$-alkyl, a $C_2$-$C_6$-alkenyl, a $C_3$-$C_6$-cycloalkyl, a $C_1$-$C_4$-alkylthio-$C_1$-$C_4$-alkyl, a $C_1$-$C_4$-halogenoalkylthio-$C_1$-$C_4$-alkyl having 1 to 5 halogen atoms, a $C_1$-$C_4$-alkoxy-$C_1$-$C_4$-alkyl, a $C_1$-$C_4$-halogenoalkoxy-$C_1$-$C_4$-alkyl having 1 to 5 halogen atoms, and a phenyl optionally substituted by a halogen atom, a $C_1$-$C_4$-alkyl, a $C_1$-$C_4$-alkoxyalkyl, or a nitro group;
- $R^1$ is selected from the group consisting of a hydrogen atom, a $C_1$-$C_6$-alkyl group, and a $C_3$-$C_7$-cycloalkyl;
- $R^2$ is a $C_1$-$C_6$-alkyl group;
- $R^3$ is selected from the group consisting of a hydrogen atom, and a $C_1$-$C_6$-alkyl group;
- each X is independently selected from the group consisting of a hydrogen atom and a $C_1$-$C_6$-alkyl group;
- W is selected from the group consisting of a carbon atom and a silicon atom, provided that, if W is carbon, $R^{41}$ is hydrogen and $R^{42}$ is not a substituted or unsubstituted phenyl;
- $R^4$, $R^5$ and $R^6$ are independently selected from the group consisting of a hydrogen atom, a halogen atom, and a $C_1$-$C_6$-alkyl group, at least two of the substituents $R^4$, $R^5$ and $R^6$ being different from a hydrogen atom; or two of the substituents $R^4$, $R^5$ and $R^6$ may together form a 3-, 4-, 5- or 6-membered non aromatic carbocyclic ring optionally substituted with a $C_1$-$C_6$-alkyl group;

as well as its salts, N-oxides, and optically active isomers.

2. The compound of claim 1 wherein $R^2$ is a methyl group.

3. The compound of claim 2 wherein:
- $R^1$ is hydrogen;
- $R^3$, $R^4$, $R^5$ and $R^6$ are independently selected from the group consisting of a hydrogen atom and a methyl group;
- each substituent X is independently selected from the group consisting of a hydrogen atom and a methyl group; and
- $R^{40}$ is a $C_1$-$C_4$-halogenoalkyl having 1 to 5 halogen atoms.

4. The compound of claim 1 wherein $R^{40}$ is selected from the group consisting of a halogen atom, a $C_1$-$C_4$-alkyl, a $C_1$-$C_4$-halogenoalkyl having 1 to 5 halogen atoms, a $C_1$-$C_4$-halogenoalkoxy having 1 to 5 halogen atoms, and a $C_1$-$C_4$-alkyloxy.

5. The compound of claim 1 wherein $R^4$, $R^5$ and $R^6$ are independently selected from the group consisting of a hydrogen atom and a methyl group.

6. The compound of claim 1 wherein each substituent X is independently selected from the group consisting of a hydrogen atom and a methyl group.

7. The compound of claim 1 wherein said compound is of the structural formula:

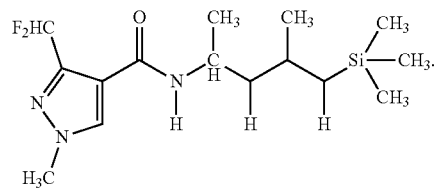

8. The compound of claim 1 wherein said compound is of the structural formula:

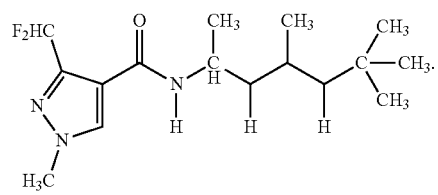

9. The compound of claim 1 wherein W is a silicon atom.

10. The compound of claim 1 wherein W is a carbon atom.

11. A fungicide composition comprising an effective amount of the compound of claim 1 and an agriculturally acceptable support.

12. A method for combating the phytopathogenic fungi of crops comprising applying an effective and non-phytotoxic amount of the composition of claim 11 to the plant seeds or to the plant leaves and/or to the fruits of the plants or to the soil in which the plants are growing or in which it is desired to grow them.

* * * * *